Figure 1:
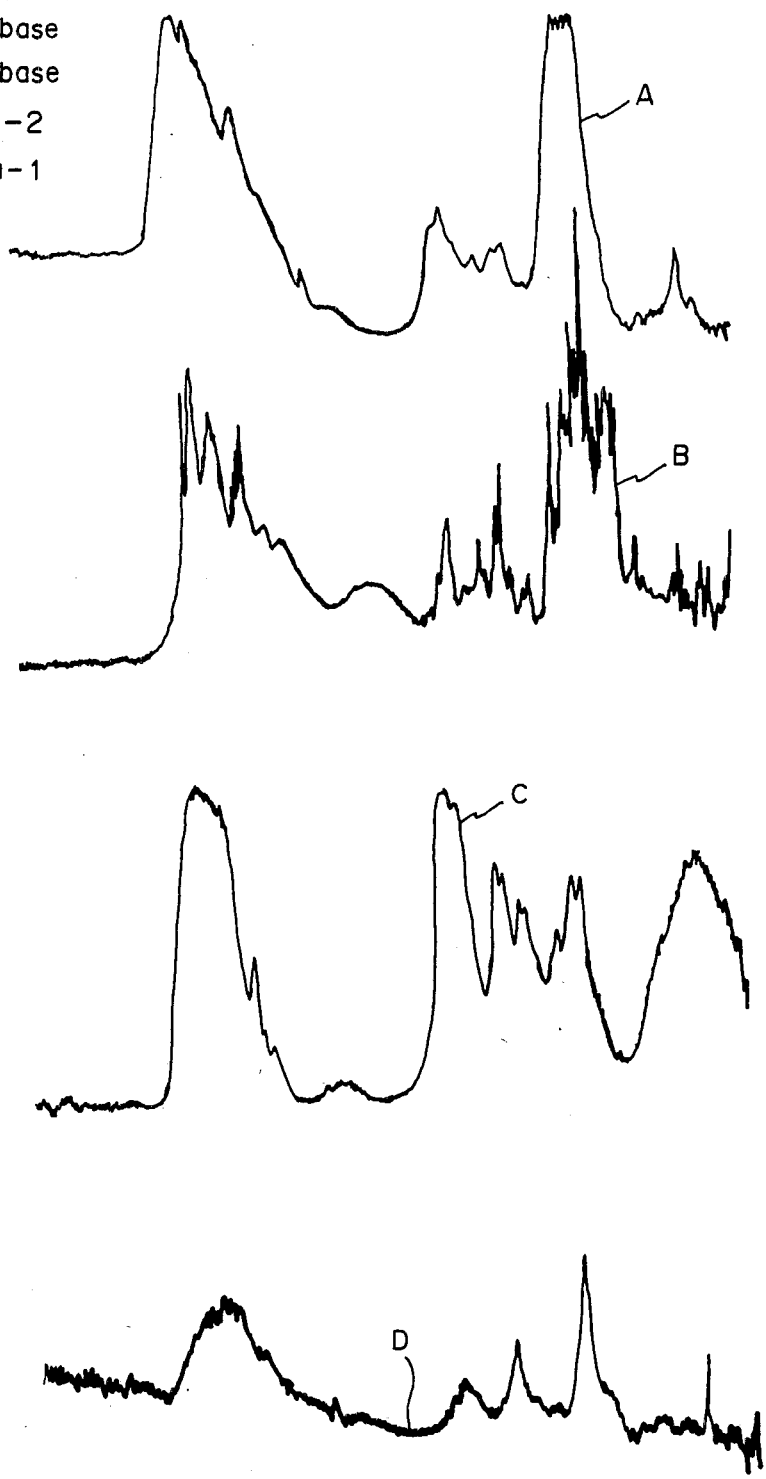

United States Patent [19]

Pierson

[11] Patent Number: 4,645,760

[45] Date of Patent: Feb. 24, 1987

[54] ACTIVATED AMINOGLYCOSIDES AND AMINOGLYCOSIDE-AMINOCYCLITOLS PHARMACEUTICAL COMPOSITIONS AND METHOD OF USE

[75] Inventor: Martha Pierson, Delmar, N.Y.

[73] Assignee: Health Research Inc., Albany, N.Y.

[21] Appl. No.: 516,117

[22] Filed: Jul. 20, 1983

Related U.S. Application Data

[63] Continuation-in-part of Ser. No. 403,703, Jul. 30, 1982, abandoned.

[51] Int. Cl.$^4$ .................. A61K 31/71; C07H 15/232
[52] U.S. Cl. ........................................ 514/39; 436/95;
514/36; 514/37; 514/40; 514/41; 536/13.2;
536/13.3; 536/13.5; 536/13.6; 536/13.7;
536/16; 536/16.1; 536/16.8; 536/124

[58] Field of Search .............. 424/180, 181; 536/13.2,
536/13.3, 13.5, 13.6, 13.7, 16.8, 16, 16.1, 124;
514/36, 37, 39, 40, 41

[56] References Cited

U.S. PATENT DOCUMENTS 3,896,238  7/1975  Smith .................................. 424/181
4,029,883  6/1977  Hiraga et al. ...................... 536/13.3

Primary Examiner—Johnnie R. Brown
Attorney, Agent, or Firm—Jacobs & Jacobs

[57] ABSTRACT

Aminoglycosides and aminoglycoside-aminocyclitols which have been oxygen-radical activated show a broad spectrum of antibacterial activity. The activated compounds are able to penetrate the cell membranes of bacteria and show substantially enhanced activity as compared to the parent unactivated compound.

13 Claims, 2 Drawing Figures

ACTIVATED AMINOGLYCOSIDES AND AMINOGLYCOSIDE-AMINOCYCLITOLS PHARMACEUTICAL COMPOSITIONS AND METHOD OF USE

This is a continuation-in-part of my application Ser. No. 403,703 filed July 30, 1982, now abandoned.

The present invention is concerned with aminoglycosides and aminoglycoside-aminocyclitols which have been oxygen-radical activated with the result that the activated compounds produced have a broad spectrum of antibacterial activity. The activated compounds are able to penetrate the cell membranes of bacteria and show substantially enhanced activity as compared to the parent compound.

Aminoglycosides and aminoglycoside-aminocyclitols are classes of compounds known in the art (see for example, "Comparative Chemistry of Aminoglycoside and Aminocyclitol Antibiotics" by K. L. Rinehart and R. M. Stroshane, "Biosynthesis of Aminocyclitol Antibiotics", *The Journal of Antibiotics* (1976) Vol. 29, pp. 319–353; K. L. Rinehart, "Comparative Chemistry of the Aminoglycoside and Aminocyclitol Antibiotics", *Journal of Infectious Disease* (1969) Vol. 119, pp. 345–350; M. A. Sande and G. L. Mandell, "The Aminoglycosides" in Goodman and Gilman's *The Pharmacological Basis of Therapeutics*, Sixth Edition, Chapter 51; and A. G. Gilman, L. S. Goodman and A. Gilman, Eds Macmillan, Inc., New York 1980, pp. 1162–1180; Umezawa, S.: "Structures and Synthesis of Aminoglycoside Antibiotics" in *Advances in Carbohydrate Chemistry and Biochemistry*, Vol. 30, R. S. Tipson and D. Horton, Ed. Academic Press, NY, NY 1974, pp. 111–182; Umezawa, S.: "The Chemistry and Conformation of Aminoglycoside Antibiotics" in *Drug Action and Drug Resistance in Bacteria*, Vol. 2, *Aminoglycoside Antibiotics*, S. Mitsuhashi, Ed., University Park Press, Tokyo, 1975, p. 3–43.) These compounds are known to have primary amino groups. It has how been discovered that these compounds are free radical scavangers and hence would be useful as anti-inflammatory agents and antioxidants. Before activation, these compounds exhibit only a limited range of anti-bacterial activity, generally against gram negative bacteria.

The present invention resides in the surprising discovery that aminoglycosides and aminoglycoside-aminocyclitols can be oxygen-activated. This activation is performed with an oxygen-free radical. The superoxide and/or hydroxyl radicals are suitable activators. The reactions can be conducted in-vitro in both cell-free and cell-containing media.

The activated compound resulting therefrom appears to be less polar than the parent compound, displays enhanced solubility in non-polar solvents which enables it to more easily penetrate cell membranes, thereby permitting oral administration of the compound as well as enhancing its antibacterial activity not only against gram negative bacteria, but against gram positive, acid-fast and anaerobic bacteria. In contrast to the parent compound, i.e. before activation, the activated compound is substantially devoid of any anti-inflammatory activity. The activated compound is believed to be particularly useful as an antibacterial agent because of its enhanced rate of uptake. It maintains its high affinity for the 30S ribosomal sub-unit.

The present invention also includes a process for the activation of aminoglycosides and aminoglycoside-aminocyclitols, pharmaceutical compositions containing such activated compounds as the therapeutically active agent and to methods of treating bacterial infections in humans and animals which comprises administering such activated compounds for the treatment of bacterial infections.

The present invention also includes the surprising discovery that aminoglycosides and aminoglycoside-aminocyclitols have anti-inflammatory properties and are useful for the treatment of inflammation in humans and animals. Thus the compounds are also useful for reducing or minimizing inflammation which occurs during radiation therapy or chemotherapy employing radiomimetic chemical agents, i.e. agents that produce oxygen-free radicals. These compounds may be formulated into pharmaceutical compositions by combining an anti-inflammatory amount or a therapeutically effective amount of an aminoglycoside or an aminoglycoside-aminocyclitol in combination with a pharmaceutically acceptable carrier. The composition may then be administered by the conventional routes of administration to humans and animals for the treatment of inflammation or for the reduction or minimization of inflammation by administering a therapeutically effective amount of the composition to a human or animal in need thereof.

According to one embodiment of the present invention, aminoglycosides and aminoglycoside-aminocyclitols are activated by reacting the parent compound with a source of oxygen-free radicals such as, for example, with hydroxyl radicals, superoxide radicals or singlet oxygen radicals in an environment which stabilizes the radical. A suitable environment would include high pH, high oxygen tension and the presence of iron cations. The presence of protein may also be desirable as a stabilizer.

According to another embodiment of the present invention, neomycin is characterized by being soluble in non-polar solvents after incubation in the presence of an enzymatic reaction which generates $O_2$ and OH but substantially insoluble prior to enzymatic reaction and being further characterized by being less soluble in water after modification than before.

The molecular weight of the activated compounds does not differ significantly from the parent compound. The activated compounds of the present invention are also reducing agents, due to their activation; that is, they are in a partially oxidized state.

Suitable sources of superoxide, hydroxyl and other active oxygen species include, but are not limited to, the following:

Generators of $O_2$ and OH

A. Enzymatic
  1. Radicals released directly into aqueous solution
     a. flavoenzymes such as xanthine oxidase
     b. flavoenzyme dehydrogenase
     c. aldehyde dehydrogenase
     d. dihydroorotic dehydrogenase
     e. glutathione reductase
  2. Radicals stabilized within the enzyme core (not released freely)
     a. flavoprotein-dependent hydroxylases
        1. p-hydrobenzoate hydroxylase
        2. orcinol hydroxylase
        3. salicylate hydroxylase
        4. metahydroxy benzoate-4-hydroxylate
     b. pteridine-dependent hydroxylase 1. phenylalanine hydroxylase
2. tyrosine hyroxylase
   c. Cytochrome P450-dependent hydroxylases
      1. camphor methylene hydroxylase
      2. NADPH-dependent cytochrome P450 reductase
   d. Iron-sulphur protein-dependent hydroxylases
   e. 2-ketoglutarate-dependent hydroxylases
      1. proline hydroxylase
      2. lysine hydroxylase
   f. Copper-containing hydroxylases
      1. dopamine $\beta$-hydroxylase
      2. phenolases
   g. other
      1. cysteamine oxygenase
      2. anthranilate hydroxylase
      3. ethionamine sulphoxidase
      4. p-coumaric acid hydroxylase
      5. 2-nitropropane oxygenase
      6. peroxidase
B. Photochemical
   1. Spontaneous reoxidation of photoreduced flavins in presence of hydrogen donor
      a. riboflavin
      b. flavin adenine dinucleotide (FAD)
      c. flavin mononucleotide (FMN)
   2. Photolysis of water, hydrogen peroxide, hydroquinones, melanins, quinones, leucoflavins (FMNH or FADH), catecholamines, thiols, tetrahydropteridines, pyrogallol, ferrohemoproteins, iron sulphur proteins (ferrodoxin, adrenodoxin, putidaredoxin, rubridoxin), NADH with phenazine methosulphate and ascorbate.
C. Chemical
   1. Spontaneous, or catalyzed autooxidations of: hydroquinones, melanins, quinones, leucoflavins (FMNH or FADH), catecholamines, thiols, tetrahydropteridines, pyrogallol, ferrohemoproteins, iron sulphur proteins (ferrodoxin, adrenodoxin, putidaredoxin, rubridoxin), NADH with phenazine methosulphate and ascorbate.
   2. hydroxylation of dihydroxyfumarate in presence of ascorbate.
D. Electrochemical
   1. By univalent cathodic reduction of molecular oxygen; recovery necessitates an aprotic solvent or surfactant on electrodes.
   2. univalent oxidation of hydrogen peroxide; recovery necessitates an aprotic solvent or surfactant on electrodes.
E. Radiolysis of oxygenated aqueous solutions, hydrogen peroxide, hydroquinones, melanins, quinones, leucoflavins (FMNH or FADH), catecholamines, thiols, tetrahydropteridines, pyrogallol, ferrohemoproteins, iron sulphur proteins (ferrodoxin, adrenodoxin, putidaredoxin, rubridoxin), NADH with phenazine methosulphate and ascorbate.
F. Ultrasonication of aqueous solutions of E.
G. Solutions of salts of $O_2$ in protic and aprotic solvents
   1. Tetrabutyl ammonium superoxide salts
   2. potassium superoxide
   3. tetraalkyl ammonium superoxide
H. Biological sources such as aerobically respiring cells, leucocytes and bacteria.

The reactions using radiolysis of oxygenated aqueous solutions, ultrasonification of aqueous solutions and solutions of salts of $O_2$ in aprotic solvents (E, F and G above) produce the greatest concentrations of $O_2$ and $OH^-$. Stabilizing the radicals increases the concentration. One useful stabilization procedure utilizes a high pH. However, since the parent compounds themselves tend to degrade at a pH of about 10–13, it is best to achieve a balance among the $O_2$ and $OH^-$ concentrations, the stability of the parent compound and the percent conversion to activated compound.

Biological sources such as bacteria (H above) are useful for producing activated compounds of the present invention. According to one procedure found to be useful, a suitable bacterium is incubated in the presence of the parent compound to the point at which the antibacterial potency of the filtrate is enhanced. The bacterium is then removed leaving the filtrate. The filtrate was then tested against a suitable organism such as *B. subtilis* and substantial enhancement of antibacterial potency as compared to the parent compound was observed.

The following aminoglycosides may be activated according to the present invention:
1. kanamycins, amikacin and seldomycins
2. gentamicins and sisomycins
3. neomycins, aurimycin, lividomycins, paromomycins, streptothricins, hybrimycins, coralinomycin, butirosin
4. streptomycins and streptomutins
5. nebramycins and tenebrimycins
6. netilmicins
7. ribostamycins
8. destomycins
9. trehalosamines
10. myomycins
11. fortimicins
12. mutamicins
13. kasugamycin, and
14. aminoglycosides which are highly basic and water soluble such as:
    B-2847-Alpha H
    G-418, G-52
    JI-20A
    NK-1001, -1003, -1012-1, -1012-2, -1012-3, NK-1013-1, and -1013-2
    1160
    66-40D (See H. Umezawa, Index of Antibiotics from Actinomycetes, Vol. II (1978).)

The oxygen radical reactivity of 4-aminoglycosides KM, streptomycin (SM), neomycin (NM), and gentamicin (GM) was tested using a previously described modification of the commonly used epinephrine autoxidation assay. The results in the table below show that aminoglycosides compete with epinephrine for active oxygen and that they do so in the rank order KM≧SM>NM>GM (relative molar ratio for 50% inhibition ~6:6:2:1). These results may indicate differences in the aminoglycosides' reaction rates with oxygen radicals, or in the number of sites available for reaction on each molecule. Further studies are required to determine the identification of the reacting active oxygen species (e.g. singlet oxygen, hydroperoxy radicals, superoxide radicals, hydroxyl radicals, or others). Nonetheless, epinephrine autoxidation was blocked 97% when a fourfold molar excess of KM was used, which suggests a reactivity with other active oxygen species as well as superoxide radicals since superoxide dismutase (SOD) itself blocks epinephrine autoxidation by a maximum of only about 80%.

The table below demonstrates the effectiveness of four aminoglycosides in inhibiting the autoxidation of epinephrine. Reactions were performed at 25° C.; in 0.1M sodium carbonate, pH 10.2. Absorbance at 320 nm ($A_{320}$) as measured with a Varian model 219 spectrophotometer. Antibiotics (Sigma) were used in the sulfate form; the working molecular weight reflects the anhydrous weight of the base. At least five aminoglycoside concentrations, each replicated four times, were used to estimate the 50% epinephrine autoxidation inhibition value. Epinephrine concentrations yielding between 0.23 and 0.27 $\Delta A_{320}$ per minute was the basis for calculating the percent of inhibition. The data were analyzed by linear regression; standard deviations are shown.

| Drug | Working molecular weight | (A) Molarity for 50% inhibition (M × $10^3$) | (B) Epinephine molarity (M × $10^3$) | B/A Molar ratio |
|---|---|---|---|---|
| KM | 666 | 0.70 ± 0.10 | 0.78 ± 0.01 | 1.11 |
| SM | 1650 | 0.74 ± 0.10 | 0.80 ± 0.01 | 1.08 |
| NM | 963 | 2.10 ± 0.14 | 0.82 ± 0.01 | 0.39 |
| GM | 455 | 4.40 ± 0.46 | 0.83 ± 0.01 | 0.19 |

The parent compounds in the above table were subjected to two synthetic activation processes according to the present invention. As set forth below, the parent compound was incubated with $2.8 \times 10^{-5}$M riboflavin and 0.01M methionine (a hydrogen donor) for a half hour in the presence of a uv light. The potency of the mixture of activated compound and parent compound recovered was as follows:

| Parent Compound | KM | SM | NM | GM |
|---|---|---|---|---|
| enhancement | 25% | 18% | 100% | 167% |

In the second synthetic activation process, xanthine oxidase was incubated with $5 \times 10^{-3}$M xanthine and 10 umg/ml of parent compound. Under those conditions, the following conversion for parent compound occurred:

| Parent Compound | KM | SM | NM | GM |
|---|---|---|---|---|
| conversion | 6.8% | 4% | 19.3% | 25.8% |

The above data suggests that all reactive sites of an aminoglycoside-aminocyclitol react with hydroxyl and/or superoxide free radicals, thus resulting in enhanced antibacterial activity for the activated compound. It is possible that the reaction rates of individual sites may vary. Antibacterial activity would be enhanced, but to a lesser extent when partial completion of such reactions occur.

Activation of neomycin B base by incubation in aqueous xanthine oxidase and xanthine resulted in the production of an identifiable novel activated compound. This activated compound unlike the parent compound absorbed well in the uv region, was soluble in DMSO and had a retardation factor of about 0.7 compared to 0.1 for neomycin B base [cellulose F plate; solvent=n-propanol: pyridine: acetic acid: water (15:10:3:12)]. The activated compound was also a reducing agent.

When neomycin B base was reacted with potassium superoxide in water, several activated antibiotically active compounds were obtained. In the first four hours, three activated compounds were obtained, all having retardation factors of less than 0.32. All can be stained with ninhydrin. When the reaction is allowed to continue for several days, other novel antibiotics are formed and the original three are difficult to detect. The newly formed ones have $R_f$'s of 0.40, 0.53, 0.74 and 0.84, using the above cellulose F thin layer chromatographic system.

It has been found that coincubation of superoxide dismutase with aminoglycosides (gentamicin, kanamycin) and bacteria (*E. coli, Pseudomona aeruginosa*) prevents the killing of bacteria (in a concentration dependent manner) by aminoglycosides. Since this extra-cellular SOD catalyzes the dismutation of superoxide radicals (only extra-cellularly), it is inferred that a reaction of aminoglycosides and $O_2$ or $OH\cdot$ free radical in the extra-cellular space is necessary before bacterial kill can occur due to aminoglycosides. The mechanism of blockade is believed to be a prevention of aminoglycoside uptake. The reaction of oxygen-free radicals with aminoglycosides is thought to effectively neutralize polar $NH_2$ groups, thus facilitating transmembrane diffusion. Catalase in combination with SOD increases this blockade ten-fold. Catalase blockade occurs alone. The inference is that hydroxyl radicals, as well or even rather than $O_2$ is the mediating activator of aminoglycoside and aminoglycoside-aminocyclitol compounds.

These conclusions are based on the accepted rationale that reactions requiring superoxide or hydroxyl radicals are both blocked by SOD, while reactions requiring hydroxyl radicals are blocked by catalase, which degrades hydrogen peroxide and thereby prevents the Haber-Weiss type reaction of reaction (2) below. This rationale can also be visualized chemically as follows: (1) for the dismutation of $O_2$ and for (2) the generation of $OH\cdot$ via the Haber-Weiss type reaction:

  (1)

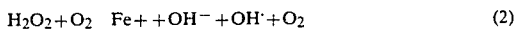  (2)

Bacteria themselves can be expected to generate $O_2$ extracellularly. Thus, bacteria may activate aminoglycosides and aminoglycoside-aminocyclitols as long as they are in active aerobic respiration. If a bacterium is aerobic, is incapable of enzymatically inactivating aminoglycosides or aminoglycoside-aminocyclitols and yet is resistant to them due to a lack of ribosomal affinity, the bacteria would provide an externally useful activating system.

The present invention also includes a method of assaying concentrations of aminoglycosides and aminoglycoside-aminocyclitols which comprises the steps of (1) providing a source of oxygen-free radicals; (2) providing a substrate which undergoes a colorimetric change due to oxygen-radical-mediated oxidation, reduction, substitution or addition; (3) means for monitoring this colorimetric change; (4) maintaining a desired pH; (5) measuring the rate of this colorimetric change in the presence of a known volume of a sample of the aminoglycoside or aminoglycoside-aminocyclitol (of unknown concentration); (6) comparing this latter rate to a standardized curve of colorimetric blockage for aminoglycoside or aminoglycoside-aminocyclitol solutions of known concentration at the same pH; and (7) determining the amount of aminoglycoside or aminoglycoside-aminocyclitol present in the unknown sample. The identity of the aminoglycoside or aminoglycoside-aminocyclitol being assayed must be known.

The auto-oxidation of epinephrine is blocked on a mole-to-mole basis by aminoglycosides and aminoglycoside-aminocyclitols. It also has been found that the reduction of nitro-blue tetrazolium dye in the presence of a source of superoxide-free radicals can be blocked by such compounds. Moreover, it has been found that hydroxyl spin adducts formed with either N-oxyl or nitroso spin trapping agents are blocked by the aminoglycoside-aminocyclitols as determined by Electron Paramagnetic Resonance. Other colorimetric or chemiluminescence assays for superoxide or hydroxyl radicals which use dyes or other reagents that can develop color selectively in the presence of these radicals can also form the basis of rapid photometric assays for parent aminoglycoside and aminoglycoside-aminocyclitol levels in biological or other aqueous solutions. The degree to which colored products are blocked by the aminoglycoside or the aminoglycoside-aminocyclitol compound would be directly proportional to the concentration of aminoglycosides and aminoglycoside-aminocyclitol compounds. Representative dyes and reactants include the following non-limitative list:

| REACTANT | PRODUCT | METHOD |
|---|---|---|
| Tetrazolium salts | Formazan (by reduction) | SP 560 nm |
| Ferricytochrome C | Ferrocytochr.C (reduct) | SP 550 nm |
| acetylated $Fe^{+5}$ cyt.C | Ferrocytochr.C (reduct) | SP 550 nm |
| Tetranitromethane | Nitroform anion (reduct) | SP 350 nm |
| Epinephrine | Adrenochrome (oxidation) | SP 310,485 nm |
| Sulfite | Sulfate (oxidation) | SP 235 nm (bleach) |
| Hydroxylamine | nitrite (oxidation) | SP 530 nm |
| Luminol | aminophthalate (oxidat) | Chemiluminescence |
| p-nitrosodimethyl aniline | OH* adduct | SP 440 nm (bleach) |
| N—oxyl compounds | Spin trap adduct | E.P.R. |
| Tiron | Semiquinone | E.P.R. |

SP = spectrophotometry
E.P.R. = electron paramagnetic resonance

The following non-limitative examples more particularly illustrate the present invention:

EXAMPLE 1

Neomycin B base (NMb) and potassium superoxide ($KO_2$) were added to double distilled dimethylsulfoxide (DMSO). The suspension was vigorously stirred for several days in a nitrogen atmosphere. After 92 hours, both of the DMSO- insoluble products, NMb and $KO_2$, had disappeared into solution. The solution was spotted on cellulose tlc plates eluted in 15:10:3:12 n-propanol:-pyridine:acetic acid:water. A single compound was observed which could be stained with ninhydrin (a stain for primary amino groups). None of the original NMb could be detected. This novel compound has an Rf of 0.7 in this system. The novel compound is antibiotically active (tested by the disc diffusion method against B. subtilis-seeded agar plates) after low temperature rotary evaporation of the DMSO followed by resuspension in water. The product tests positive with Fehling's reagent suggesting the presence of an aldehyde or some other reducing moiety. The ninhydrin stain was brown suggesting both imino and amino groups are present.

EXAMPLE 2

The procedure of Example 1 was repeated except that 1,4 dioxane was used as the solvent. A single new antibiotic with the same Rf of 0.70 was produced. The antibiotic nature of the compound was established by biological assay.

EXAMPLE 3

NMb base was incubated with an enzymatic source of oxygen-free radicals, xanthine and xanthine oxidase. This led to the formation of two novel antibiotics. One had an Rf of 0.65 to 0.70 and the second had an Rf of from 0.40 to 0.43. The antibiotic activity of the two compounds was established by biological assays.

Preparatory tlc plates were used to partially purify and isolate the compounds produced. The purified materials were resuspended in water and tested against B. subtilis by disc diffusion tests. Both of the novel antibiotics produced blue-brown ninhydrin spots suggesting they possess amino as well as possible imino groups. The compound with an Rf=0.7 tests positive by Fehling's test suggesting an aldehyde or some other reducing moiety. It reduces nitroblue tetrazolium, sustaining the conclusion that the parent compound was oxidized during activation, but that it is not fully oxidized.

EXAMPLE 4

Powdered potassium superoxide was added directly to an aqueous solution of NMb sulfate. Within four hours three new antibiotics were produced. None had an Rf higher than 0.32. One of them produced a bright yellow ninhydrin stain, one of them produced a brown ninhydrin stain and one of them produced a blue ninhydrin stain. Bioassay of the compounds demonstrated biological activity.

EXAMPLE 5

A solution of $2.8 \times 10^8 M$ riboflavin, and a hydrogen donor such as 0.01M methionine, was irradiated with ultraviolet light at 365 nm for a half hour to produce oxygen-free radicals. When aminoglycosideaminocyclitol compounds were coincubated in this system, a solution was produced that was more potent that the parent (riboflavin-free) solution produced in the same manner. The enhanced potency resulting from coincubation of gentamicin neomycin, kanamycin and streptomycin was shown using the antibiotic disc diffusion tests employing B. subtilis-seeded agar plates.

EXAMPLE 6

When the unactivated aminoglycosides, NMb, GM, or KM, are added to a cuvette containing a source of superoxide free radicals (photoreduced riboflavin or xanthine-xanthine oxidase) as well as the superoxide free radical detector, oxidized nitro-blue tetrazolium (NBT), the rate of NBT reduction is slowed proportionally to the concentration of aminoglycoside. This is spectrophotometrically monitored at 560 nm, where the maximum absorbance of reduced NBT occurs. This procedure decreases in sensitivity at pH's higher than 7.0 and at very high (millimolar) drug concentrations. The reason for these limits is that superoxide reacts with aminoglycosides to generate a reducing compound which can interfere with the assay by directly reducing NBT. Within a range of low aminoglycoside concentrations and a low pH, a linear blockade as a function of concentration can be demonstrated.

In a similar manner, vancomycin, polymixens and cycloserine can also be assayed.

EXAMPLE 7

When the unactivated aminoglycoside-aminocyclitol compounds are added at pH=10.2 to a cuvette containing epinephrine and 0.1 molar carbonate buffer, the aminoglycosides block the autoxidation of epinephrine to adrenochrome on approximately a mole-to-mole basis. This blockade is monitored spectrophotometrically at 320 nm and is a linear function of drug concentration. Using $9 \times 10^{-4}$ molar epinephrine, the linear region extends from $10^{-5}$ to $10^{-3}$ molar aminoglycoside. The sensitivity of this assay can be extended by lowering the starting epinephrine concentration.

EXAMPLE 8

When neoomycin B sulfate, kanamycin sulfate or streptomycin sulfate are added in millimolar concentrations to reaction mixtures containing a source of hydroxyl free radicals and a hydroxyl free radical spin trap, the formation of a hydroxyl free radical spin-adduct is prevented in a concentration-dependent manner. Two spin traps were examined with the same conclusion, nitrosotertiary-butyl (ntb) and 5,5-dimethyl-1-pyrroline-1-oxide. The reaction mixture used to produce hydroxyl radical included $10^{-4}$M xanthine, $6 \times 10^{-8}$M xanthine oxidase, $10^{-3}$ EDTA, $10^{-4}$M spin trap (DMPO or ntb), $8.9 \times 10^{-5}$M $H_2O_2$, 0.1M potassium phosphate buffer; final pH—7.8. The free radical signals were directly monitored with and without the antibiotics by using the techniques of Electron Paramagnetic Resonance starting 2 minutes after reaction initiation. The scan range=100 Gauss; time constant=0.064 sec; modulation amplitude=1 Gauss; Microwave power=1 Mw; Microwave frequency=9.418 GHz; Field set=3350 Gauss; scan time=20 seconds; modulation frequency=100 KHz. $A_H = A_N = 14.9$ G.

EXAMPLE 9

If, according to the procedure of Example 4, the reaction is not stopped after four hours but allowed to continue for several days, a different novel antibiotic precipitates from the solution upon acidification to pH6.5. Initial precipitation begins after about four days with the amount precipitating tending to maximize after five days. If the reaction is allowed to continue beyond five days only a small further amount continues to precipitate out.

In place of pH adjustment, the novel compound can also be extracted from the aqueous solution by partitioning with chloroform. Following the partitioning, however, the compound readily precipitates out of solution. The chloroform-solubility reflects an extraordinary change from the solubility characteristics of NMb. The rapid loss of solvency probably reflects a high lability of an interesting intermediate of the novel compound described below. Lowering of pH apparently oxidizes the compound. It also apparently readily oxidizes in air. Prior to oxidation, the compound is antibiotically active against *E. coli, Staph. aureus, Ps. aeruginosa, Ps. malto-philia, Ps. pickettii*, and *B. subtilis*. After air oxidation, it is not soluble in chloroform but is soluble in DMSO. It has a UV absorbance peak at 267 nm. It stains with ninhydrin and has a retardation factor of 0.74 on a cellulose F plate developed in n-propanol: pyridine: acetic acid: water (15:10:3:12).

When the above reaction is repeated with a high concentration of neomycin B base, a group of antibiotically active substances are produced, none of which appear to be the above novel compound. Three novel compounds were identified. One substance has an absorption peak at 337 nm. It stains strongly with ninhydrin and using the above TLC system exhibits a retardation factor of 0.84. This substance is soluble in DMSO, has a lesser solubility in water than NM b sulfate and is only slightly soluble in chloroform. The other two substances, as a mixture, stain weakly with ninhydrin and exhibit retardation factors in the above TLC system of 0.43 and 0.54. The solubility of the mixture in water is about 0.1 volume/volume water. Aqueous solutions of the mixture have UV absorption peaks at 280 and 325 nm. The mixture exhibits antibiotic activity against *B. subtilis*.

EXAMPLE 10

Following the procedure of Example 9, but using neomycin B base prepared by adding $Ba(OH)_2.8H_2O$ to neomycin B sulfate with the resultant filtrate being lypholized and used, and the reaction being quenched after a delay of 1 month 6N HCl followed by subsequent addition of 3M sodium sulfite, a novel antibiotic was formed. The quenched reaction mixture was taken to an almost dry state using a rotary evaporator. The resultant material was then extracted with 100% methanol. The undissolved material was dried using rotary evaporation, was mixed with 10 gm silica gel 60 along with water and was again rotary evaporated to dryness. The material was packed above a silica gel column (90 gm silica gel 60, 35–70 mesh ASTM) having the dimensions of 24.7 cm $\times$ 2.54 cm. Including an initial 400 ml fraction eluted with 100% methanol and fourteen 100 ml, fractions eluted with methanol:water:acetic acid (90:10:1), the first fifteen fractions were pooled, rotary evaporated as before, loaded on the same type of column and in the same manner as above and rechromatographed. This time, following an initial 200 ml elution with 100% methanol, the third subsequent fraction eluted with methanol:water:acetic acid (90:10:1) was collected. This fraction contained the compound 4 MM 0500a-1. The fraction was further purified using a silica gel G 1500 thin layer chromatography plate in a preparatory fashion. As so-purified the compound is called 4 MM 0500a-2. The infrared spectra of compounds 4 MM 0500a-1 and 4 MM 0500a-2 are shown in FIG. 1. These are probably infrared spectra of the antibiotic in salt form. The ultraviolet spectrum of 4 MM 0500a-1 exhibits peaks at 264 and 322 nm. Bactericidal data, thin layer chromatographic data, and bioautographic data are set forth in tables 1 and 2 below.

TABLE 1

| Bactericidal potency[3], kinetics and spectrum of 3 antibiotics. | mm inhibition zone due to 40 μgm/disc organism-*Bacillus subtilis*[2] | mm inhibition zone *B. subtilis*[1] per log concentration antibiotic[3] | nn inhibition zone due to 40 μgm/disc organism - *E. Coli* (ATC 25922)[1] | mm inhibition zone, *E. Coli* per log concentration antibiotic[3] | mm inhibition zone due to 40 μgm/disc coccus aureus (ATCC 25923)[1] |
|---|---|---|---|---|---|
| 4 MM 0500a-1 | 21.1 | 9.1 | 14.3 | 9.5 | 16.0 |
| Neomycin B base | 23.3 | 5.6 | 14.9 | 5.5 | 17.2 |
| Neomycin A base (neamine) | 33.8 | 7.0 | 24.7 | 7.8 | 29.8 |

TABLE 1-continued

| Bactericidal potency[3], kinetics and spectrum of 3 antibiotics. | mm inhibition zone, S. aureus per log concentration antibiotic[3] | mm inhibition zone due to 40 μgm/disc organism - Pseudomonas aeruginosa (ATCC 22853)[1] | mm inhibition zone, log concentration log concentration antibiotic[3] | mm inhibition zone due to 40 μgm/disc organism - Pseudomonas maltophilispp.[1] | mm inhibition of P. malto-philia per log conc.[3] |
| --- | --- | --- | --- | --- | --- |
| 4 MM 0500a-1 | 9.3 | 0 | — | 0 | — |
| Neomycin B base | 6.1 | 10.7 | — | 8.3 | — |
| Neomycin A base (neamine) | 9.4 | 0 | — | 0 | — |

[1] 9 ml antibiotic #5 agar (Difco), was poured warm into 15 × 100 mm Plastic petri dishes and seeded with test bacteria to a density of 2 × 10[6] bacteria per ml (except B. subtilis which was seeded as in item 2 below). Quarter inch sterile filter discs were placed on the agars and loaded with 20 microliters of test solutions at concentrations of 2000 and 200 ppm. The antibiotic amounts therefore were 40 micrograms/disc or 4 micrograms/disc. Slopes were based on duplicate tests of each substance at these two concentrations. All substances, each at two concentrations were tested on each plate. Data were averaged.

[2] 9 ml antibiotic #5 media (Difco), seeded to a concentration of 0.25 microliters of B. subtilis spores/500 ml agar, was dispensed into 15 × 100 ml plastic petri dishes. One quarter inch Schleicher and Schuell sterile filter discs were placed on the agar and loaded with 20 microliters of dilutions of test compound including dilutions of 2000 ppm, 600 ppm, 200 ppm, 60 ppm, and 20 ppm. The plates were incubated overnight at 30 degrees centigrade, the inhibition zones measured at 18hours. All values were based on 6 tests at a given concentration; each plate was corrected to an average kill zone due to 20 microliters of neomycin B base at a concentration of 30 ppm. Slopes and kill zones for 40 microgram-loaded discs were obtained using regression analysis.

[3] Concentration of compound 4 MM 0500a-1 was adjusted to represent the total organic content. That is, 2000 ppm means 2000 parts organic material per million parts water.

TABLE 2

| Retardation factors of three antibiotics using Thin Layer Chromatography of 3 sorts and a bioautograph | $R_f$ in system 1 F+ = fluorescent, N+ = ninhydrin reaction | $R_f$ in system 2 F+ = fluorescent N+ = ninhydrin reaction | $R_f$ in system 3 F+ = fluorescent N+ = ninhydrin reaction | $R_f$ range of bactericidal band eluted from system 3 preparatory plate 4 |
| --- | --- | --- | --- | --- |
| 4 MM 0500a-1 | 0.34 (N+, F+) | 0.57 (N+, F+) | 0.56 (N+, F+) | 0.53–0.67 |
| neomycin B base | 0.11 (N+, F−) | 0.09 (N+, F−) | 0 | — |
| neomycin A base (neamine) | 0.19 (N+, F−) | 0.15 (N+, F−) | 0 | — |

[1] 6.6 microgram of the three test substances (sample 4 MM 0500a-1 was adjusted to an organic content of 2000 ppm) were spotted at ¼ inch intervals on a 20 × 20 cm glass, 0.1 mm cellulose F plate, using a Gelman spotting guide and 3.3microliter disposable micropipettes. Plates developed to a height of 12 cm using 1-propanol:pyridine:acetic acid:water (15: 10: 3: 12). The compounds were visualized as fluorescent-quenching or ninhydrin-reacting spots.

[2] Samples adjusted to 2000 ppm as above, spotted as above, developed to the same height as above, on a cellulose F plate as above, but solvent mixture was methanol:water: formic acid (100:50:1). Detection as above.

[3] Samples adjusted to 2000 ppm as above, spotted as above, developed to the same height as above, but was using a plate having 0.25 mm silica gel G 1500 as an adsorbant and the solvent was methanol:water (90:10). Detection was as natural fluorescence or using ninhydrin reaction.

[4] A 20 × 20 cm glass silica gel 1500 G plate was run in solvent system 3 above. Fraction 4 MM 0500a-1 at 2000 ppm (adjusted to organic content) was spotted as a continuous series of 3.3 microliter spots in a 15 cm band, 1 inch from bottom of plate. The plate was developed to a height of 13 cm. Silica was scraped off plate in 8 bands, one of which as a control, included the baseline where neomycin B base and neomycin A base would be located if present. The scraped silica was then eluted with approximately 10 ml distilled water, rotary evaporated to a 0.5 ml volume and assayed using 10 microliter samples pipetted into wells in B. subtilis seeded agars (see footnote #2, table 1). Only the band shown in table 2, showed activity.

The antibiotic potency of compound 4 MM 0500a-1, adjusted to 2000 ppm organic content, is roughly equivalent to that of neomycin B base against subtilis, E. coli, and S. aureus. However the bactericidal spectrum of activity is more like neomycin A base since neither of two Pseudomonas species was inhibited. The biokinetics of bactericidal activity (mm kill zone/log concentration) is like that of neomycin A base against S. aureus, but is unique compared to either neomycin B base or neomycin A base in the instances using B. subtilis or E. coli. The infrared spectrum shown in FIG. 1 clearly indicates a molecular relationship to both neomycin B base or to neomycin A base, but is unique which indicates a molecular modification. The retardation factor of the the compound using thin layer chromatographic system #1 (see footnotes, table 2) is such that the compound might be mistaken for neomycin A base, but the $R_f$ is actually 10% higher, being 0.34.

The $R_f$'s of compound 4 MM 0500a-1 in systems #2 and #3 (see footnotes, table 2 are unmistakably unique compared to the $R_f$'s of either neomycin B base or neomycin A base and respectively are 0.57 and 0.56. When mixed with neomycin B base or neomycin A base, the new antibiotic appears to interact in a manner which has the effect of increasing their retardation factors in system #3 to higher values. In all thin layer chromatographic systems, the compound, 4 MM 0500a-1, is found to possess fluorescence and to stain with ninhydrin. A bioautograph demonstrates that only a single antibiotic compound exists in this column fraction and which can be eluted with water from a preparatory TLC plate of type #3 (see table 1). This antibiotic emerges in a band within the range of retardation factors of 0.53 and 0.67.

The antibiotic potency of 4 MM 0500a-2 decays rapidly due to ultraviolet exposure. The infrared spectrum of 4 MM 0500a-2 is shown in FIG. 1. The $R_f$'s of 4 MM 0500a-2 in thin layer chromatographic systems #1, 2 and 3 are respectively: 0.31, 0.56 and 0.59.

EXAMPLE 11

Figure 2:
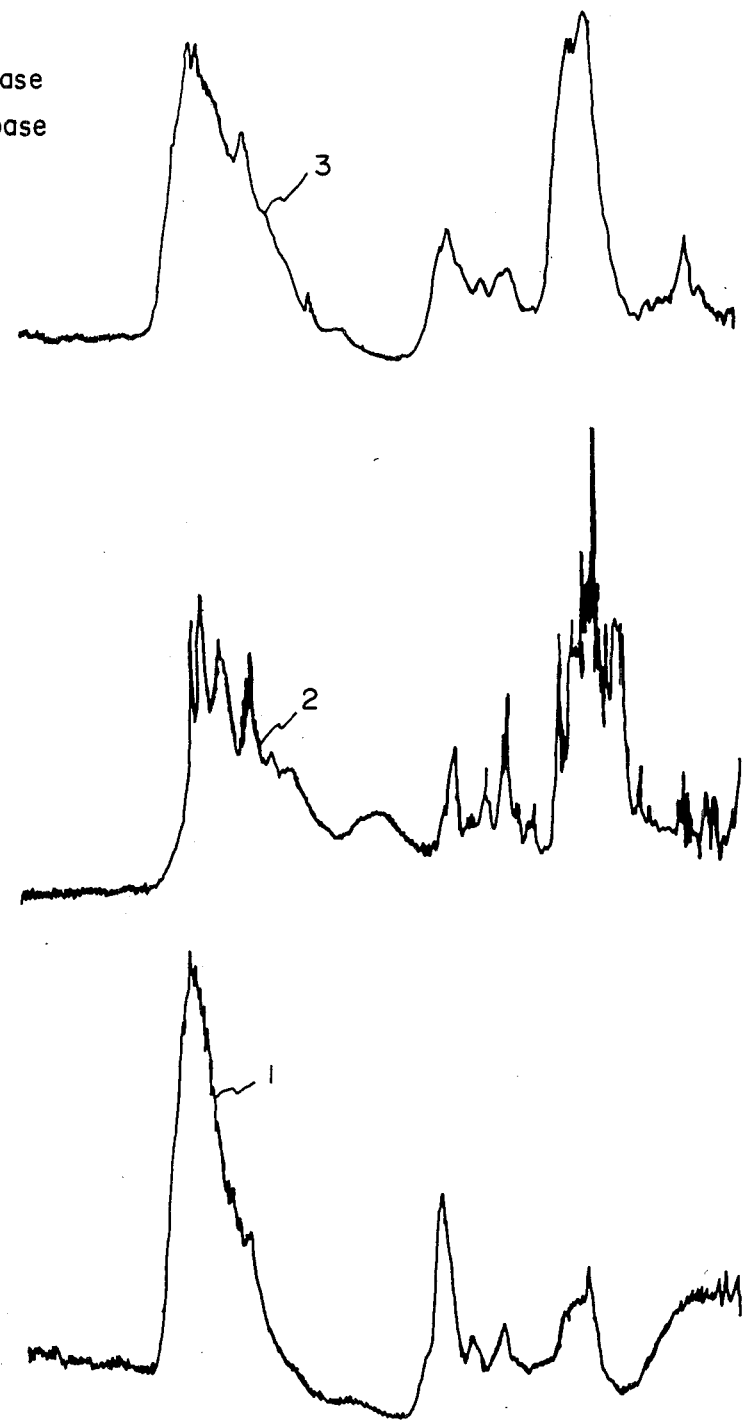

Following the procedure of Example 9 but preparing neomycin B base as in Example 10, the reaction was allowed to run for 7 days at which time the solution demonstrated a preponderance of compounds having high retardation factors relative to retardation factors characteristic of either neomycin B base or neomycin A base. At that time, the reaction mixture was lypholized to dryness. The dried material was sequentially extracted with chloroform, chloroform:ethanol (50:50), and 100% ethanol. Upon standing covered (to prevent evaporation) for two days, a precipitate falls out of the latter two extracts. These precipitates were pooled and made into an aqueous slurry with 15 gm (wet weight) silica gel 60 (35–70 mesh ASTM); the slurry was rotary evaporated to dryness. This dried material was placed on a 29 cm×2.54 column containing 150 gm (wet weight) silica gel 60 (35–70 mesh ASTM). The sixth 40-ml fraction eluted with methanol:water (75:25) contained compound 4M 0600-1. The infrared spectrum of 4M 0600-1 is shown in FIG. 2. 4M 0600-1 is believed to be in the form of the free base. The compound is basic and water soluble, although less water soluble than neomycin B base. The compound is fluorescent and reacts to generate a purple derivative with ninhydrin. The compound exhibits retardation factors using thin layer chromatographic systems #1, 2 and 3 (described in footnotes of table 2) respectively of 0.31, 0.54 and 0.54. This compound exhibts antibiotic activity against *B. subtilis*.

What is claimed is:

1. An aminoglycoside or an aminoglycoside-aminocyclitol which has been oxygen radical-activated at at least one of the primary amino sites therefor and which has anti-inflammatory activity and poor solubility in non-polar solvents before oxygen radical-activation, but which is subsequently devoid of anti-inflammatory activity and which is more soluble in non-polar solvents and which exhibits bacteriocidal activity after oxygen radical activation.

2. A compound according to claim 1 having a high affinity for the 30S Ribosomal subunit.

3. A compound according to claim 1 which is an activated aminoglycoside or aminoglycoside-aminocyclitol is soluble in non-polar solvents after incubation in the presence of any reaction which generates $O_2$ and OH but substantially insoluble in non-polar solvents prior to an oxygen radical reaction and is less soluble in water after modification than before.

4. A pharmaceutical composition useful for treating bacterial infections in humans and animals which comprises a therapeutically effective amount of an oxygen radical-activated aminoglycoside or an oxygen radical-activated aminoglycoside-aminocyclitol according to claim 1, in combination with a pharmaceutically acceptable carrier.

5. A method of treating bacterial infections in humans and animals which comprises administering to a human or animal in need thereof a therapeutically effective amount of an oxygen radical-activated aminoglycoside or an oxygen radical-activated aminoglycoside-aminocyclitol according to claim 1 in combination with a pharmaceutically acceptable carrier.

6. An aminoglycoside or an aminoglycoside-aminocyclitol which has been oxygen radical-activated at at least one of the primary amino sites therefor produced by reacting an aminoglycoside or an aminoglycoside-aminocyclitol with potassium superoxide in an aqueous medium for about four hours and isolating the substance produced.

7. An antibacterial composition of matter which has been oxygen radical-activated at at least one of the primary amino sites therefor produced by reacting neomycin B base with potassium superoxide in an aprotic or non-polar medium for from about 4 to about 6 days and isolating the agent produced.

8. An antibacterial composition of matter according to claim 7 wherein the medium is 1,4-dioxane or dimethyl sulfoxide.

9. An aminoglycoside or an aminoglycoside-aminocyclitol which has been oxygen radical-activated at at least one of the primary amino sites therefor produced by heating a high concentration of an aminoglycoside or aminoglycoside-aminocyclitol with potassium superoxide in an aqueous medium for up to one month and recovering the substance which precipitates out or which can be partitioned into non-polar solvents.

10. A pharmaceutical composition useful for treating bacterial infections in humans and animals which comprises a therapeutically effective amount of an oxygen radical-activated aminoglycoside or an oxygen radical-activated aminoglycoside-aminocyclitol according to claim 2, in combination with a pharmaceutically acceptable carrier.

11. A pharmaceutical composition useful for treating bacterial infections in humans and animals which comprises a therapeutically effective amount of an oxygen radical-activated aminoglycoside or an oxygen radical-activated aminoglycoside-aminocyclitol according to claim 3, in combination with a pharmaceutically acceptable carrier.

12. A method of treating bacterial infections in humans and animals which comprises administering to a human or animal in need thereof a therapeutically effective amount of an oxygen radical-activated aminoglycoside or an oxygen radical-activated aminoglycoside-aminocyclitol according to claim 2 in combination with a pharmaceutically acceptable carrier.

13. A method of treating bacterial infections in humans and animals which comprises administering to a human or animal in need thereof a therapeutically effective amount of an oxygen radical-activated aminoglycoside or an oxygen radical-activated aminoglycoside-aminocyclitol according to claim 3 in combination with a pharmaceutically acceptable carrier.

* * * * *